(12) United States Patent
Borries et al.

(10) Patent No.: US 10,350,090 B2
(45) Date of Patent: Jul. 16, 2019

(54) MODULAR PROXIMAL BODY TRIAL

(71) Applicant: Zimmer, Inc., Warsaw, IN (US)

(72) Inventors: Paul Borries, Columbia City, IN (US); Robert D. Krebs, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 795 days.

(21) Appl. No.: 14/960,536

(22) Filed: Dec. 7, 2015

(65) Prior Publication Data

US 2016/0158028 A1 Jun. 9, 2016

Related U.S. Application Data

(60) Provisional application No. 62/088,874, filed on Dec. 8, 2014.

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61F 2/30* | (2006.01) |

(52) U.S. Cl.
CPC .......... *A61F 2/4684* (2013.01); *A61F 2/4637* (2013.01); *A61F 2002/30332* (2013.01); *A61F 2002/30364* (2013.01); *A61F 2002/30367* (2013.01); *A61F 2002/30726* (2013.01); *A61F 2002/4641* (2013.01)

(58) Field of Classification Search
CPC ..................................................... A61F 2/4637
See application file for complete search history.

(56) References Cited

U.S. PATENT DOCUMENTS

2004/0122440 A1* 6/2004 Daniels ..................... A61F 2/36
606/102

* cited by examiner

*Primary Examiner* — Sameh R Boles
(74) *Attorney, Agent, or Firm* — Schwegman Lundberg & Woessner, P.A.

(57) ABSTRACT

A trial system for determining a suitable proximal body implant for hip replacement surgery comprises a separator instrument, a trial body attachable to a distal stem, and an insert. The insert is positioned within the trial body to receive the separator instrument. As the separator instrument is rotated about its axis, a ramp element of the insert guides a pin of the separator instrument, so as to separate the trial body from the distal stem. Additional apparatus, methods, and systems are disclosed.

14 Claims, 5 Drawing Sheets

MODULAR PROXIMAL BODY TRIAL

RELATED APPLICATIONS

This applications claims the benefit of priority to U.S. Provisional Application Ser. No. 62/088,874, filed Dec. 8, 2014, the content of which is hereby incorporated by reference in its entirety.

BACKGROUND

A human hip joint connects a femur (sometimes referred to as a thigh bone) to an acetabulum (sometimes referred to as a hip socket) of the pelvis. Hip joints support the weight of a human body, and are important for maintaining balance.

Some types of injury, disease, or degeneration can produce pain, restricted motion in the hip joint, or both. One treatment for certain types of damage to a hip joint is surgery. In some cases, the hip joint is surgically replaced.

OVERVIEW

To better illustrate the trial system disclosed herein, a non-limiting list of examples is provided here:

In Example 1, a trial system for determining a suitable proximal body implant for hip replacement surgery can be provided that includes a separator instrument, a trial body attachable to a distal stem, and an insert positioned within the trial body, wherein the insert includes a first ramp element configured to receive the separator instrument such that as the separator instrument is rotated about its axis, the first ramp element guides a first pin of the separator instrument so as to separate the trial body from the distal stem.

In Example 2, the trial system of Example 1 is optionally configured such that a distal end of the separator instrument is configured to contact a proximal end of the distal stem, such that the first ramp element facilitates separation forces between the distal end of the separator instrument and the proximal end of the distal stem.

In Example 3, the trial system of any one of or any combination of Examples 1-2 is optionally configured such that the insert is welded within the trial body.

In Example 4, the trial system of any one of or any combination of Examples 1-2 is optionally configured such that the insert is integral with the trial body.

In Example 5, the trial system of any one of or any combination of Examples 1-4 is optionally configured such that the distal stem comprises a distal stem trial.

In Example 6, the trial system of any one of or any combination of Examples 1-5 is optionally configured such that the first pin extends along an axis that is nonparallel to the axis of the separator instrument.

In Example 7, the trial system of any one of or any combination of Examples 1-6 is optionally configured such that the insert includes a second ramp element configured to guide a second pin of the separator instrument to facilitate separating the trial body from the distal stem.

In Example 8, the trial system of any one of or any combination of Examples 1-7 is optionally configured such that the trial body is attachable to the distal stem via a taper lock.

In Example 9, the trial system of any one of or any combination of Examples 1-8 is optionally configured such that the insert includes a first slot configured to receive the first pin and guide the first pin to the first ramp element.

In Example 10, the trial system of any one of or any combination of Examples 1-9 is optionally configured such that the trial body is configured to pass over a guide rod of the distal stem.

In Example 11, the trial system of any one of or any combination of Examples 1-10 is optionally configured such that the insert includes an interior passage that allows the separator instrument to pass through the insert.

In Example 12, a trial system for determining a suitable proximal body implant for hip replacement surgery can be provided that includes a separator instrument and a plurality of trial bodies, wherein the separator instrument includes a first pin, wherein each trial body of the plurality of trial bodies includes a distal portion attachable to a distal stem, a proximal portion extending from and nonparallel to the distal portion, and an insert positioned within the distal portion of the trial body, wherein the insert includes a first ramp element configured to engage the first pin of the separator instrument such that the first pin traverses the first ramp element in response to rotation of the separator instrument about its axis, thereby allowing separation of the trial body from the distal stem.

In Example 13, the trial system of Example 12 is optionally configured such that the separator instrument includes a second pin extending from and nonparallel to the separator instrument.

In Example 14, the trial system of Example 13 is optionally configured such that the insert includes a second ramp element configured to engage the second pin of the separator instrument such that the second pin traverses the ramp element in response to rotation of the separator instrument about its axis.

In Example 15, a method can be provided that includes inserting a separator instrument into an insert of a trial body attached to a distal stem, and rotating the separator instrument about its axis, such that one or more pins of the separator instrument traverse one or more ramps of the insert, creating a separation force between the trial body and the distal stem.

In Example 16, the method of Example 15 optionally includes attaching the trial body to the distal stem via a taper lock.

In Example 17, the method of any one of or any combination of Examples 15 and 16 optionally includes separating the trial body from the distal stem.

In Example 18, the method of any one of or any combination of Examples 15-17 optionally includes inserting the separator instrument into the insert of the trial body by inserting the one or more pins of the separator instrument into one or more slots of the insert, wherein the one or more slots guide the one or more pins of the separator instrument to the one or more ramps.

In Example 19, the method of any one of or any combination of Examples 15-18 optionally includes passing the trial body over a guide rod that guides the trial body onto the distal stem.

In Example 20, the method of any one of or any combination of Examples 15-19 optionally includes determining a suitable proximal body implant for hip replacement surgery based on the trial body.

In Example 21, the trial system or method of any one of or any combination of Examples 1-20 is optionally configured such that all elements or options recited are available to use or select from.

These and other examples and features of the present devices, systems, and methods will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Hip replacement surgery (hip arthroplasty) can include implantation of a distal stem into a femur of a patient, and implantation of a proximal body to connect to the distal stem. Implantable proximal bodies can be presented to a practitioner in the form of a set. The implantable proximal bodies in the set can include discrete combinations of the parameters of height (i.e., the length of the femur) and offset (i.e., the lateral distance from the central axis of the femur to the center of the femoral head in the acetabulum). Height and offset are established quantities in the field of hip replacement surgery.

In order to determine the most appropriate height and offset for a particular patient, a practitioner can use a "trial" or "provisional," which is shaped and sized similar to the implantable components, but is removable and can be reused or disposed of A practitioner can try various sizes by temporarily attaching the trial to a stem, and noting the fit of the trial with the anatomy of the patient. Once a best fit is found, the practitioner can note the values of height and offset of the trial that provides the best fit. The practitioner can then remove the trial, select an implantable proximal body from the set (the selected body having height and offset values that are closest to the noted values) and implant the selected implantable proximal body.

Figure 1:
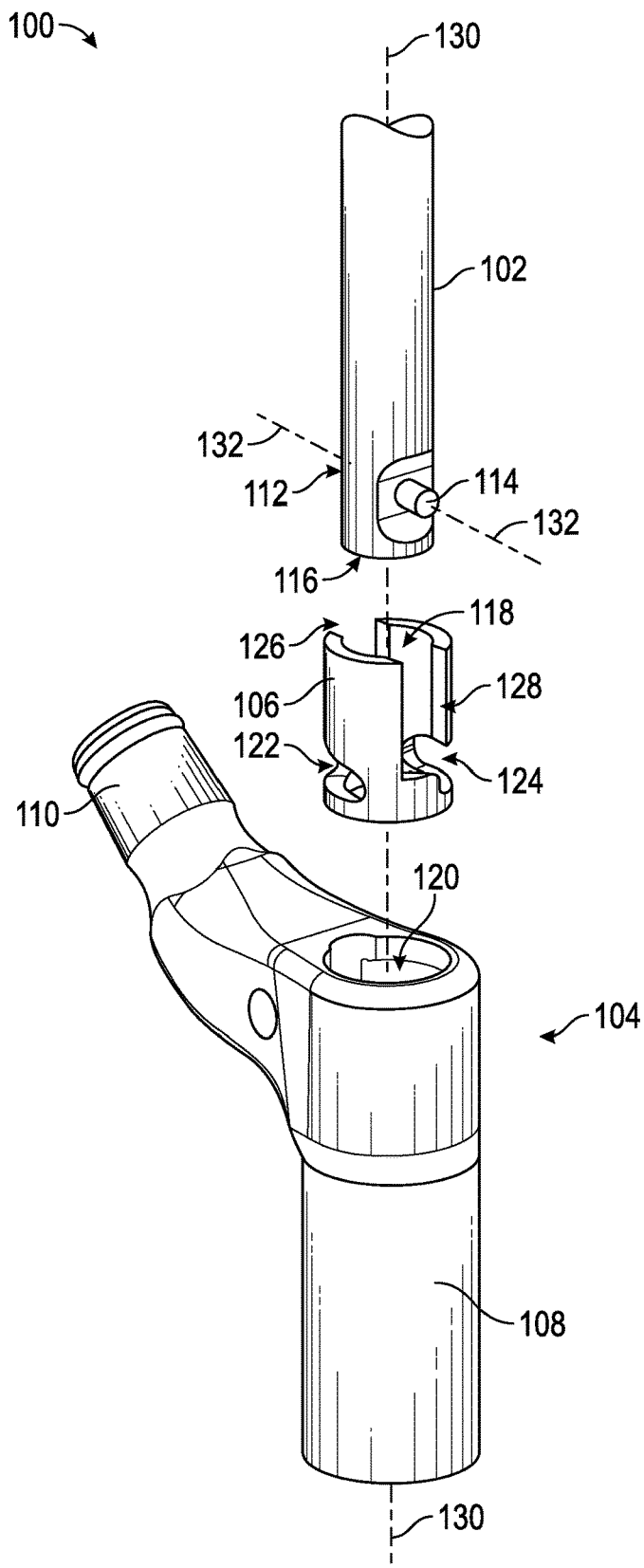
FIG. 1 is an exploded perspective view of a modular proximal body trial system, in accordance with at least one example of the present disclosure.

FIG. 1 is an exploded perspective view of a modular proximal body trial system 100, in accordance with at least one example of the present disclosure. The trial system 100 can comprise a separator instrument 102, a trial body 104, and an insert 106. A distal portion 108 of the trial body 104 is attachable to a proximal end of a distal stem. In at least one example, the distal stem can comprise a distal stem trial. In another example, the distal stem can comprise a distal stem implant. In at least one example, the distal portion 108 can be substantially cylindrical in shape, with a longitudinal axis 130 extending vertically from the proximal direction to the distal direction. In at least one example, the proximal end of the distal stem can extend into the distal portion 108 of the trial body 104. In some examples, the distal portion 108 can be dimensioned such that the trial body 104 can fit snugly, but removably, over the proximal end of the distal stem. In at least one example, the distal portion 108 of the trial body 104 can be coupled to the proximal end of the distal stem using one or more taper locks. Some distal stems can comprise a guide rod that attaches to a hole in a proximal portion of the distal stem to aid insertion into the femoral canal, guide the proximal reamer over the distal stem, and guide the proximal body trial or implant onto the distal stem. In at least one example, the distal portion 108 of the trial body 104 can be configured to pass over a guide rod of the distal stem.

The trial system 100 can further comprise a proximal portion 110. In some examples, the proximal portion 110 can extend from the distal portion 108. In at least one example, the proximal portion 110 can be nonparallel relative to the distal portion 108. The angle of the proximal portion 110 relative to the distal portion 108 can differ in various examples of the trial body 104. Various examples of the trial body 104 can comprise different combinations of height and offset. In at least one example, the trial system 100 can comprise a plurality of trial bodies 104 representing different parameters for height, offset, angle (of the proximal portion 110 relative to the distal portion 108), or a combination of these.

The separator instrument 102 can comprise one or more pins 112, 114. For example, in at least one example, the separator instrument 102 can comprise two pins 112, 114. Other examples of the separator instrument 102 can comprise more than two pins, or less than two pins. The pins 112, 114 can extend along an axis 132 that is nonparallel to the axis 130 of the separator instrument 102. In at least one example, the pins 112, 114 can be integral with the separator instrument 102. In another example, the pins 112, 114 can be formed on, or otherwise attached to the separator instrument 102. The separator instrument 102 can be generally shaped and dimensioned such that at least a distal end 116 of the separator instrument 102 passes through or fits within an interior passage 118 of the insert 106. The distal end 116 of the separator instrument 102 can be further configured to contact a proximal end of the distal stem.

The insert 106 can be positioned within an interior 120 of the trial body 104. In at least one example, the insert 106 can be coupled to the interior 120 of the trial body 104 via, for example, at least one of: a weld, adhesive, a cross pin, a friction fit, a combination of these, or the like. In at least one example, the insert 106 can be integral with the trial body 104. The insert 106 can comprise one or more ramp elements 122, 124. For example, in the illustrated example, the insert 106 can comprise two ramp elements 122, 124. Other examples of the insert 106 can comprise more than two ramp elements, or less than two ramp elements. In some examples, the number of ramp elements 122, 124 of the insert 106 can be coordinated with the number of pins 112, 114 of the separator instrument 102. In some examples, the insert 106 can comprise one or more slots 126, 128 configured to receive pins 112, 114 of the separator instrument 102 and guide the pins 112, 114 to ramp elements 122, 124 of the insert 106. In at least one example, the number of slots 126, 128 can be coordinated with the number of pins 112, 114 of the separator instrument 102. For example, in the illustrated example, the insert 106 can comprise two slots 126, 128 to coordinate with the two pins 112, 114 of the separator instrument 102, 104. Other examples of the insert 106 can comprise more than two slots or less than two slots.

The ramp elements 122, 124 of the insert 106 can be configured to receive the pins 112, 114 of the separator instrument 102 and guide the pins 112, 114 as the separator instrument 102 is rotated about its axis 130. As the separator instrument 102 is rotated about its axis 130, the pins 112, 114 can traverse the ramp elements, creating separation forces (e.g., normal forces) between the distal end 116 of the separator instrument 102 and the proximal end of the distal stem. That is, the ramp elements 122, 124 of the insert 106, in combination with the pins 112, 114 of the separator instrument 102, can facilitate separation of the trial body 104 from the distal stem. In at least one example, the separation forces created by the pins 112, 114 traversing the ramp elements 122, 124 can be sufficient to disengage a taper lock that couples the trial body 104 to the distal stem.

The direction of rotation necessary to decouple the trial body 104 from the distal stem can depend on the orientation of the ramp elements 122, 124. For example, in some examples, the ramp elements 122, 124 are oriented such that a clockwise rotation of the separator instrument 102 creates the separation forces, while in other examples, the ramp elements 122, 124 are oriented such that a counterclockwise rotation of the separator instrument 102 creates the separation forces. In at least one example, the ramp elements 122, 124 can be oriented such that either a clockwise or a counterclockwise rotation will create the separation forces. Further, various examples may employ different configurations of the ramp elements 122, 124 to affect the degree of rotation of the separator instrument 102 necessary to separate the trial body 104 from the distal stem. In at least one example, the separator instrument 102 can rotate about its axis (130) 270° or less to decouple the trial body 104 from the distal stem. In some examples, the separator instrument 102 can rotate about its axis (130) 90° to decouple the trial body 104 from the distal stem.

Figure 2:
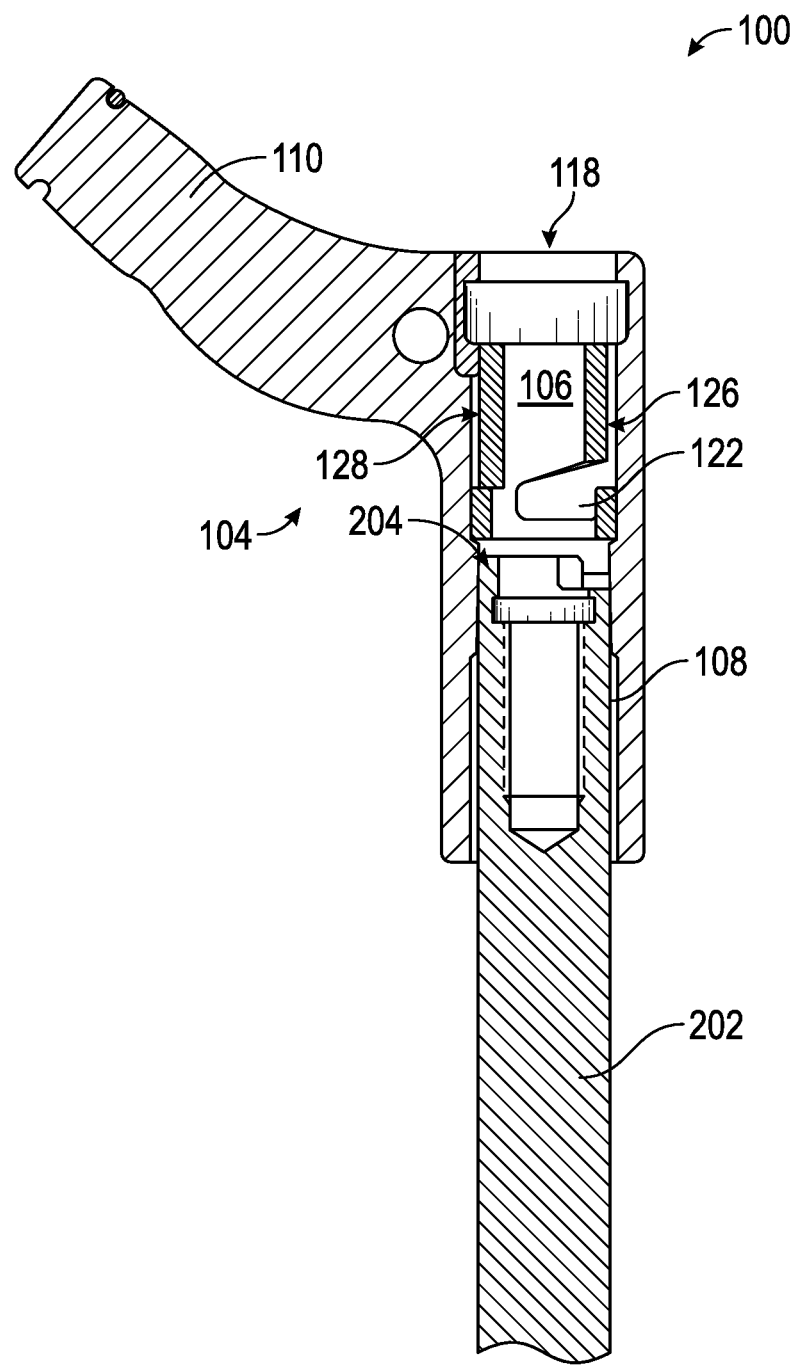
FIG. 2 is a cross-section view of a modular proximal body trial system, in accordance with at least one example of the present disclosure.

FIG. 2 is a cross-section view of the modular proximal body trial system 100, in accordance with at least one example of the present disclosure. In the illustrated example, the trial system 100 comprises the trial body 104 and insert 106 discussed above with regard to FIG. 1, along with a distal stem 202. As shown, the distal portion 108 of the trial body 104 can be fitted over the distal stem 202. In at least one example, the trial body 104 can be coupled to the distal stem 202 via a taper lock. As further illustrated in FIG. 2, the insert 106 can be positioned within the trial body 104, such that the separator instrument 102 (FIG. 1) can pass through an interior passage 118 of the insert 106 until a proximal end 204 of the distal stem 202 contacts or is positioned adjacent to the distal end 116 of the separator instrument 102. The slots 126, 128 can guide the pins 112, 114 (FIG. 1) of the separator instrument 102 to the corresponding ramp elements 122, 124 (FIG. 1) of the insert 106. Each of the trial body 104, insert 106, and separator instrument 102 can comprise any of a variety of materials. In at least one example, one or more of the trial body 104, insert 106, and separator instrument 102 comprises metal, for example, stainless steel. In some examples, one or more of the trial body 104, insert 106, and separator instrument 102 comprises a combination of materials.

Figure 3:
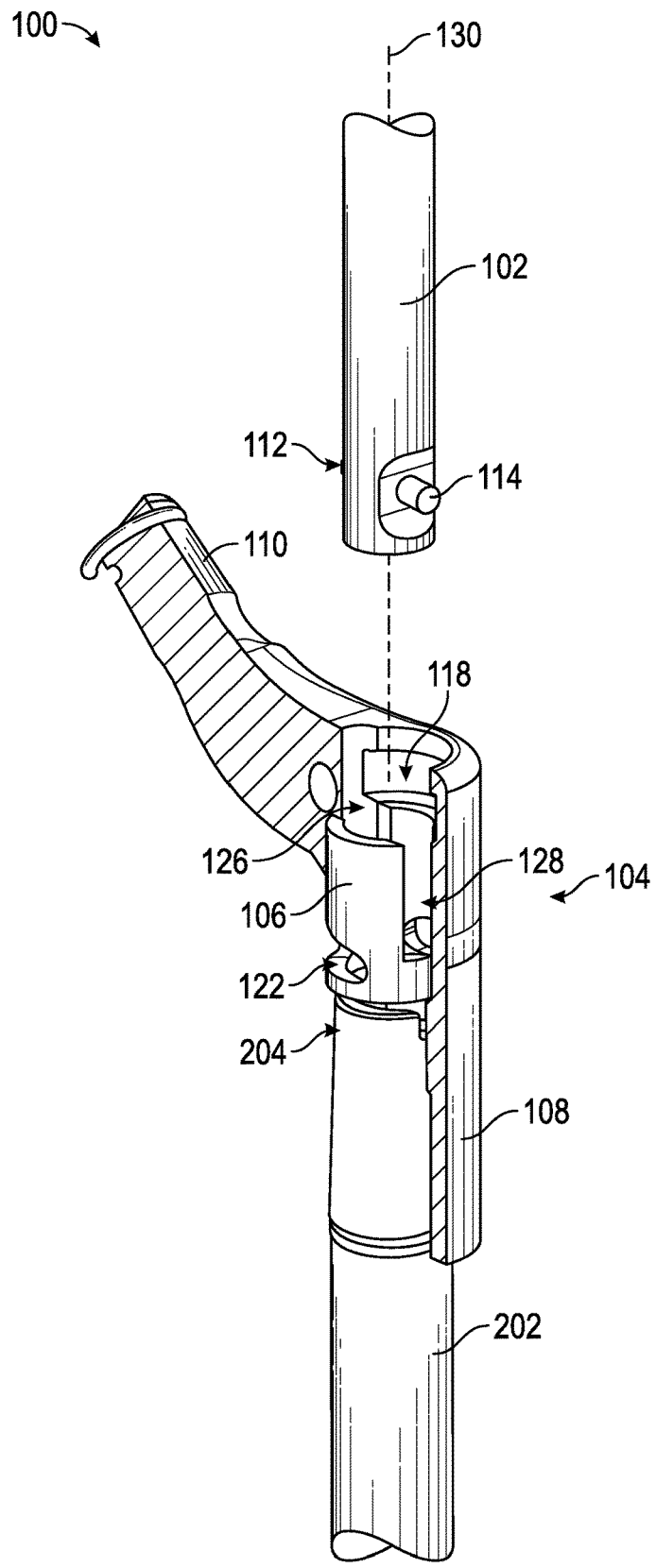
FIG. 3 is a partial cross-section view of a modular proximal body trial system before a separator instrument is inserted into a trial body, in accordance with at least one example of the present disclosure.

FIG. 3 is a partial cross-section view of the modular proximal body trial system 100 before the separator instrument 102 is inserted into the trial body 104, in accordance with at least one example of the present disclosure. As shown in FIG. 3, the distal portion 108 of the trial body 104 is coupled to the distal stem 202, and the insert 106 is positioned within the trial body 104. Prior to a separation procedure, the separator instrument 102 can be aligned with the insert 106, such that the slots 126, 128 of the insert 106 receive the pins 112, 114 of the separator instrument 102 when the separator instrument 102 is inserted into the interior passage 118 of the insert 106.

Figure 4:
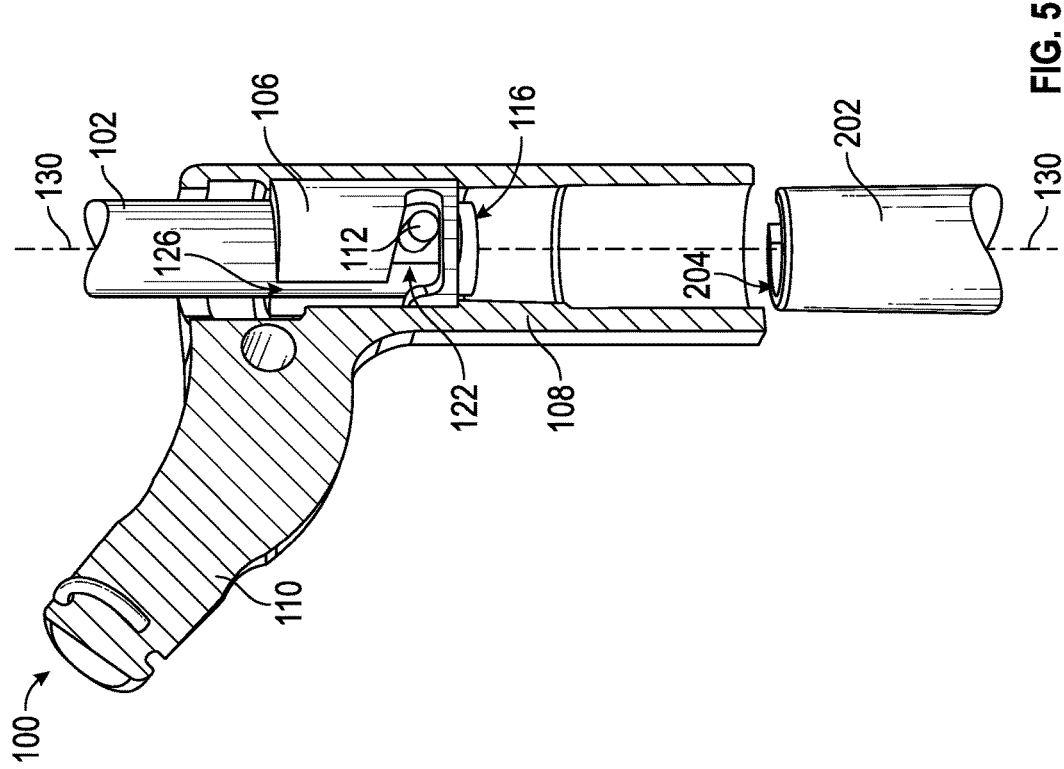
FIG. 4 is a partial cross-section view of a modular proximal body trial system with a separator instrument inserted in a first position, in accordance with at least one example of the present disclosure.

FIG. 4 is a partial cross-section view of the modular proximal body trial system 100 with the separator instrument 102 inserted in a first position, in accordance with at least one example of the present disclosure. As shown in FIG. 4, the distal portion 108 of the trial body 104 is coupled to the distal stem 202, for example, via a taper lock. In the illustrated example, the separator instrument 102 has been inserted into the interior passage 118 (FIGS. 1-3) of the insert 106, such that the slot 126 has guided the pin 112 to the ramp element 122. Although not shown, the slot 128 has guided the pin 114 to the ramp element 124. In the illustrated example, the separator instrument 102 has not yet been rotated about its axis 130 to traverse the ramp element 122 (and the ramp element 124). As such, the distal end 116 of the separator instrument 102 is in contact with the proximal end 204 of the distal stem 202, but has not yet separated the trial body 104 from the distal stem 202.

Figure 5:
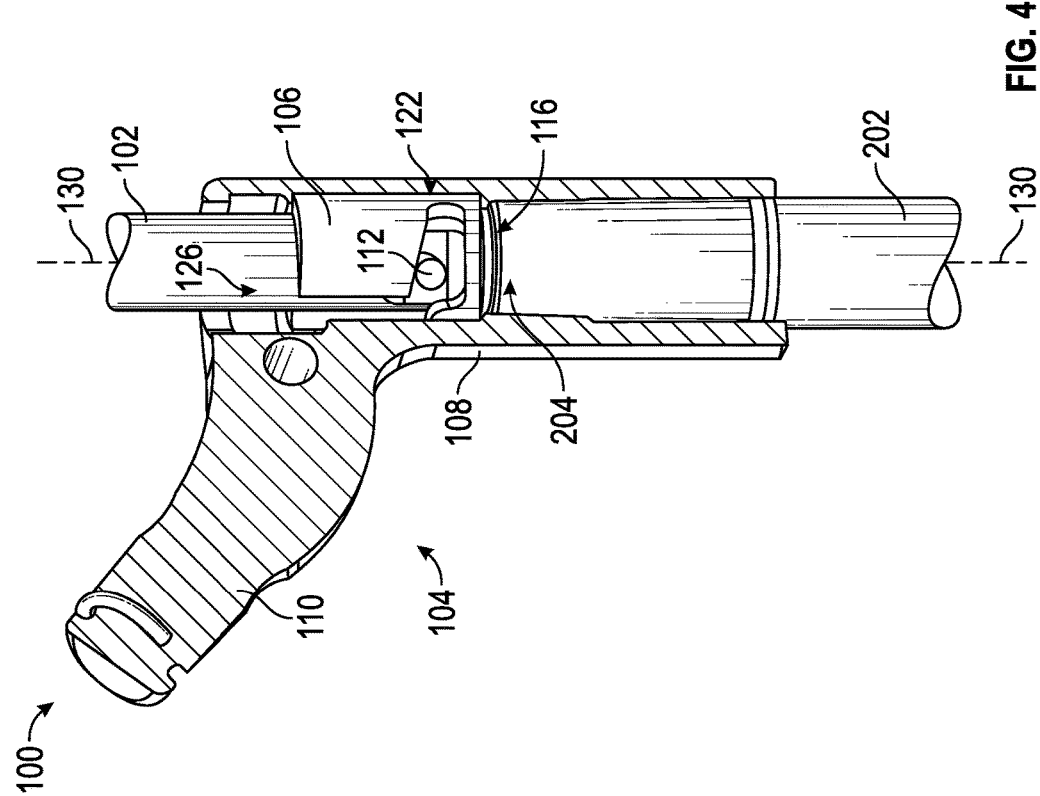
FIG. 5 is a partial cross-section view of the modular proximal body trial system of FIG. 4 after the separator instrument has been rotated about its axis, in accordance with at least one example of the present disclosure.

FIG. 5 is a partial cross-section view of the modular proximal body trial system 100, assembled as shown in FIG. 4, after the separator instrument 102 has been rotated about its axis 130, in accordance with at least one example of the present disclosure. As the separator instrument 102 rotates from its position in FIG. 4 to its position in FIG. 5, the pin 112 travels along the ramp element 122 (and the pin 114 travels along the ramp 124), such that the slope of the ramp element and the contact between the separator instrument 102 and the proximal end 204 of the distal stem 202 create a separation force that forces the trial body 104 away from the distal stem 202. The separator instrument 102 travels distally in relation to the trial body 104 as the separator instrument 102 rotates about its axis 130, until the separating force causes the trial body 104 to separate from the distal stem 202. The insert 106 remains positioned within the trial body 104 as the trial body 104 is removed from the distal stem 202.

In the illustrated example, the separator instrument 102 has been rotated about its axis 130 in a counterclockwise direction less than 180° to decouple the trial body 104 from the distal stem 202. However, in other examples, the insert 106 may be configured, such that the separator instrument 102 rotates in a clockwise direction to decouple the trial body 104 from the distal stem 202. Further, the degree of rotation of the separator instrument 102 that results in separation of the trial body 104 from the distal stem 202 may vary with other examples. In at least one example, the separator instrument 102 is removed from the insert 106 by reversing the motions of insertion. For example, in the illustrated example, the separator instrument 102 is removed by a practitioner rotating the separator instrument 102 about its axis 130 in the clockwise direction until the pin 112 is aligned with the slot 126, and then pulling the separator instrument 102 through the slot 126.

Figure 6:
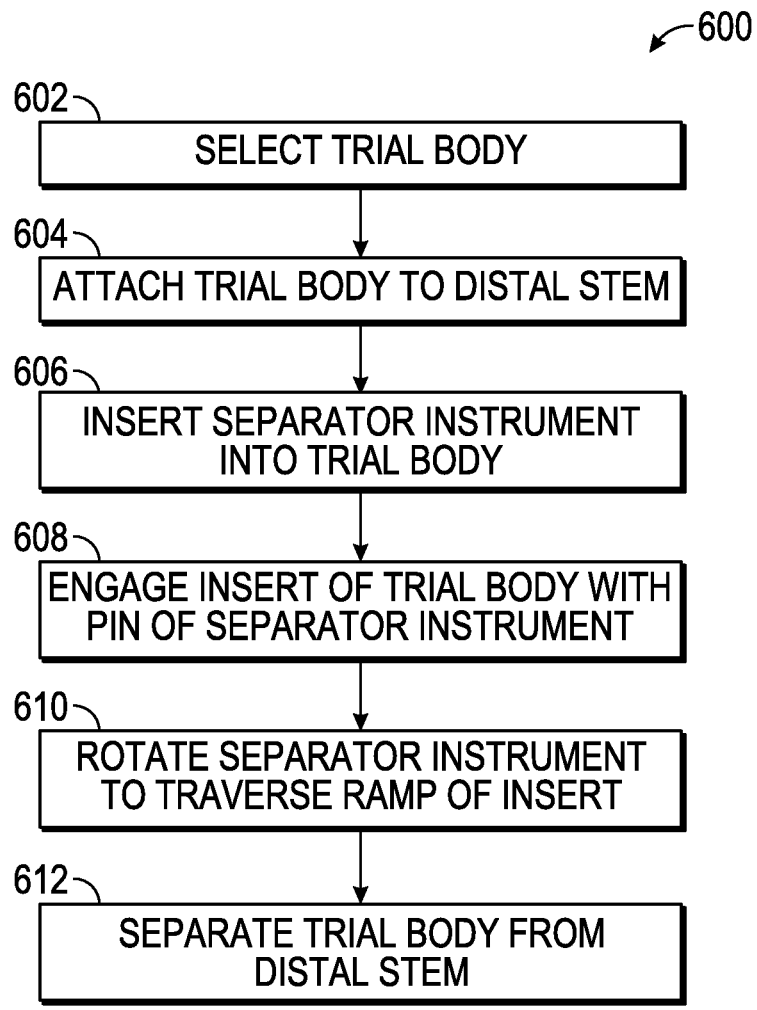
FIG. 6 is a flow chart of an example method of using the modular proximal body trial system of FIGS. 1-5, in accordance with at least one example of the present disclosure.

FIG. 6 is a flow chart of a method 600 of determining a suitable proximal body implant for hip replacement surgery, in accordance with at least one example of the present disclosure. As a matter of convenience, the method 600 is described with reference to the trial system 100 of FIGS. 1-5. At block 602, a user can select a trial body 104. For example, in at least one example, the user can select a trial body 104 from a plurality of trial bodies representing different parameters, such as height, offset, angle (of a proximal portion 110 of the trial body relative to a distal portion 108 of the trial body), or a combination of these.

At block 604, the user can attach the trial body 104 to the distal stem 202. The distal stem 202 may be a distal stem trial or a distal stem implant. In at least one example, the user can couple the trial body 104 to the distal stem 202 via one or more taper locks. In at least one example, the trial body 104 can pass over a guide rod that guides the trial body 104 onto the distal stem 202. The user can then judge the appropriateness of the parameters of the trial body 104. If the parameters of the trial body 104 are appropriate, the trial body 104 can be removed in preparation for the associated implant. If the parameters of the trial body 104 are not appropriate, the trial body 104 can be removed to attempt a different one of the plurality of trial bodies comprising different parameters.

At block 606, the user can insert the separator instrument 102 into the trial body 104 by directing the separator instrument 102 toward the distal stem 202. In at least one example, the user can align the one or more pins 112, 114 of the separator instrument 102 with one or more slots 126, 128 of the insert 106 positioned within the trial body 104. At block 608, the user can engage the insert 106 with the one or more pins 112, 114 of the separator instrument 102. The separator instrument 102 can then pass through the interior passage 118 of the insert 106 as the one or more slots 126, 128 of the insert receive the one or more pins 112, 114 of the separator instrument 102. The one or more slots 126, 128 can be configured to guide the one or more pins 112, 114 to one or more corresponding ramp elements 122, 124 of the insert 106.

At block 610, the user can rotate the separator instrument 102 about its axis 130, such that the one or more pins 112, 114 of the separator instrument 102 traverse the one or more ramp elements 122, 124 of the insert 106. The one or more pins 112, 114 traversing the one or more ramp elements 122, 124 can create a separation force between the distal end 116 of the separator instrument 102 and the proximal end 204 of the distal stem 202. The separation force causes the trial body 104 to decouple from the distal stem 202. For example, in at least one example, the separation force (e.g., a normal force) disengages a taper lock. The insert 106 may be configured such that the one or more pins 112, 114 traverse the one or more ramp elements 122, 124 when the separator instrument 102 rotates either clockwise or counterclockwise.

At block 612, the user can separate the trial body 104 from the distal stem 202. Following the rotation of the separator instrument 102, and resulting decoupling of the trial body 104 and the distal stem 202, the trial body 104 can be removed from the distal stem 202. In some examples, the user can select another trial body 104 with different parameters and repeat the method 600. The separator instrument 102 can be removed from the insert 106 by rotating the separator instrument 102 about its axis 130 in the opposite direction and pulling the one or more pins 112, 114 through the one or more slots 126, 128 away from the one or more ramp elements 122, 124.

In the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own as a separate example.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific examples. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific examples. However, the benefits, advantages, solutions to problems, and any feature(s) that may cause any benefit, advantage, or solution to occur or become more pronounced are not to be construed as a critical, required, or essential feature of any or all the claims. Moreover, the particular examples disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular examples disclosed above may be altered or modified and all such variations are considered within the scope of the disclosed subject matter. Accordingly, the protection sought herein is as set forth in the claims below.

What is claimed is:

1. A trial system for determining a suitable proximal body implant for hip replacement surgery, comprising:
    a separator instrument;
    a trial body attachable to a distal stem; and
    an insert positioned within the trial body, the insert comprising:
    a first ramp element configured to receive the separator instrument such that as the separator instrument is rotated about its axis, the first ramp element guides a first pin of the separator instrument so as to separate the trial body from the distal stem.

2. The trial system of claim 1, wherein a distal end of the separator instrument is configured to contact a proximal end of the distal stem, such that the first ramp element facilitates separation forces between the distal end of the separator instrument and the proximal end of the distal stem.

3. The trial system of claim 1, wherein the insert is welded within the trial body.

4. The trial system of claim 1, wherein the insert is integral with the trial body.

5. The trial system of claims 1, wherein the distal stem comprises a distal stem trial.

6. The trial system of any of claims 1, wherein the first pin extends along an axis that is nonparallel to the axis of the separator instrument.

7. The trial system of any of claims 1, wherein the insert further comprises:
a second ramp element configured to guide a second pin of the separator instrument to facilitate separating the trial body from the distal stem.

8. The trial system of any of claims 1, wherein the trial body is attachable to the distal stem via a taper lock.

9. The trial system of any of claims 1, wherein the insert further comprises:
a first slot configured to receive the first pin and guide the first pin to the first ramp element.

10. The trial system of any of claims 1, wherein the trial body is configured to pass over a guide rod of the distal stem.

11. The trial system of any of claims 1, wherein the insert comprises an interior passage that allows the separator instrument to pass through the insert.

12. A trial system for determining a suitable proximal body implant for hip replacement surgery, comprising:
a separator instrument comprising a first pin; and
a plurality of trial bodies, each trial body of the plurality of trial bodies comprising:
a distal portion attachable to a distal stem;
a proximal portion extending from and nonparallel to the distal portion; and
an insert positioned within the distal portion of the trial body, the insert comprising:
a first ramp element configured to engage the first pin of the separator instrument such that the first pin traverses the first ramp element in response to rotation of the separator instrument about its axis, thereby allowing separation of the trial body from the distal stem.

13. The trial system of claim 12, wherein the separator instrument further comprises:
a second pin extending from and nonparallel to the separator instrument.

14. The trial system of claim 13, wherein the insert further comprises:
a second ramp element configured to engage the second pin of the separator instrument such that the second pin traverses the ramp element in response to rotation of the separator instrument about its axis.

* * * * *